United States Patent [19]
Bednar et al.

[11] Patent Number: 6,063,584
[45] Date of Patent: May 16, 2000

[54] ANTICOAGULANT TEST

[75] Inventors: Bohumil Bednar; Robert J. Gould, both of North Wales, Pa.

[73] Assignee: Merck & Co., Inc., Rahway, N.J.

[21] Appl. No.: 08/975,312

[22] Filed: Nov. 21, 1997

[51] Int. Cl.$^7$ .................................................. G01N 33/566
[52] U.S. Cl. ...................... 435/7.21; 435/7.24; 435/7.25; 435/7.9; 435/7.94; 436/501; 436/519; 436/520
[58] Field of Search ..................... 435/7.24, 7.9, 435/7.21, 7.25, 7.94; 436/501, 519, 520

[56] References Cited

U.S. PATENT DOCUMENTS

| | | | |
|---|---|---|---|
| 4,717,654 | 1/1988 | Savoca et al. | 436/501 |
| 5,196,309 | 3/1993 | Ginsberg | 435/7.21 |
| 5,318,899 | 6/1994 | Scarborough et al. | 435/69.6 |
| 5,585,243 | 12/1996 | Aster et al. | 435/7.21 |
| 5,716,951 | 2/1998 | Blackburn et al. | 514/219 |
| 5,736,339 | 4/1998 | Scarborough et al. | 435/7.1 |

FOREIGN PATENT DOCUMENTS

WO 95/08116   3/1995   WIPO .

OTHER PUBLICATIONS

S.A. Mousa et al., Drugs of the Future, vol. 21, No. 11, 1141–1154, 1996.

Curtis et al., Blood, "Antibodies in Sulfonamide–Induced Immune Thrombocytopenia Recognize . . . ", vol. 84(1), pp. 176–183 (1994).

Visentin et al., Transfusion, "Detection of drug–dependent, platelet–reactive antibodies by antigen–capture ELISA and flow cytometry", vol. 30(8), pp. 694–700 (1990).

Newman, Peter J. and Nathalie Valentin, Thrombosis and Haemostatis, "Human Platelet Alloantigens: Recent Findings, New Perspectives", vol. 74(1), pp. 234–239 (1995).

Skogen et al., Transfusion, "Rapid determination of platelet alloantigen genotypes by polymerase chain reaction using allele–specific primers", vol. 34(11), pp. 955–960 (1994).

McFarland et al., Blood, "Neonatal Alloimmune Thrombocytopenia Due to a New Platelet–Specific Alloantibody", vol. 81(12), pp. 3318–3323 (1993).

Kunicki, Thomas J. and Peter J. Newman, Blood, "The Molecular Immunology of Human Platelet Proteins", vol. 80(6), pp. 1386–1404 (1992).

*Primary Examiner*—Mary E. Ceperley
*Attorney, Agent, or Firm*—Richard S. Parr; Melvin Winokur

[57] ABSTRACT

The present invention is a method for identifying a patient at risk to developing fibrinogen receptor antagonist-induced thrombocytopenia which comprises incubating patient plasma with a GPIIb/IIIa receptor:GPIIb/IIIa receptor antagonist complex to form a GPIIb/IIIa receptor:GPIIb/IIIa receptor antagonist:plasma antibody complex, incubating the GPIIb/IIIa receptor:GPIIb/IIIa receptor antagonist: plasma antibody complex with a secondary anti-human detectable antibody to form a GPIIb/IIIa receptor:GPIIb/IIIa receptor antagonist:plasma antibody:secondary anti-human detectable antibody complex, and detecting the presence of the secondary anti-human detectable antibody in the GPIIb/IIIa receptor:GPIIb/IIIa receptor antagonist:plasma antibody:secondary anti-human detectable antibody complex.

6 Claims, No Drawings

ANTICOAGULANT TEST

BACKGROUND OF THE INVENTION

Drug-induced thrombocytopenia contributes to morbitity and, occasionally, mortality in patients treated with a wide range of medications Karpatkin, Am. J. Med. Sci. 262:68 (1971)). More than 100 different medications have been implicated in drug-induced thrombocytopenia, including heparin, quinine, quinidine and sulfonamide antibiotics (Shulman et al. Hemostasis and Thrombosis (ed 2) Philadelphia, Pa., Lippincott (1987) p.452, and Kracke et al. JAMA 122:168 (1943).

Drug-dependent antibodies reactive with platelets have been identified in only a few instances. Curtis et al., Blood, vol. 84, no.1 (Jul. 1) 1984: pp. 176–183, applied flow cytometry to the detection of such antibodies induced by sulfonamide antibiotics. Visentin et al. Transfusion Oct. 30, 1990 (8) pp. 694–700 describes detection of drug-dependent, platelet-reactive antibodies by antigen-capture ELISA and flow cytometry.

The present invention is a means for identifying, in a patient, the presence of one or more antibodies in GP IIb/IIIa receptor (fibrinogen receptor) antagonist-induced thrombocytopenia which recognize GPIIb/IIIa receptor:GPIIb/IIIa receptor antagonist complexes formed with purified platelets or purified GPIIb/IIIa receptor and a selected GPIIb/IIIa receptor antagonist. Identification of such antibodies identifies the patient as being at risk to development of thrombocytopenia resulting from administration to the patient of the selected GP IIb/IIIa receptor antagonist

SUMMARY OF THE INVENTION

The invention is a method for identifying a patient at risk to developing fibrinogen receptor antagonist-induced thrombocytopenia resulting from treatment of the patient with a selected fibrinogen receptor antagonist, which comprises reacting patient plasma with a GPIIb/IIIa receptor:GPIIb/IIIa receptor antagonist complex to form a first reaction product, reacting the first reaction product with a secondary anti-human detectable antibody to form a second reaction product, and detecting in the second reaction product the level of binding between the secondary anti-human detectable antibody and the GPIIb/IIIa receptor:GPIIb/IIIa receptor antagonist complex. An indication that the secondary anti-human detectable antibody binds to the GPIIb/IIIa receptor:GPIIb/IIIa receptor antagonist complex indicates the presence of interaction between the GPIIb/IIIa receptor:GPIIb/IIIa receptor antagonist complex and a patient plasma antibody. The presence of such interaction identifies the patient as at risk to developing thrombocytopenia following treatment with the selected fibrinogen receptor antagonist.

DETAILED DESCRIPTION OF THE INVENTION

In the method, the patient at risk is one who is receiving treatment to inhibit thrombosis by administration of a selected fibrinogen receptor antagonist which inhibits the binding of fibrinogen to the GPIIb/IIIa receptor.

The objective of the method is to determine whether the patient's plasma contains an antibody to the GPIIb/IIIa receptor:GPIIb/IIIa receptor antagonist complex formed when the selected fibrinogen receptor antagonist binds to the GPIIb/IIIa receptor. The GPIIb/IIIa receptor:GPIIb/IIIa receptor antagonist complex may be prepared for purposes of the method by coating commercially available GPIIb/IIIa platelet receptors, including but not limited to those on platelets or purified platelets, and GPIIb/IIIa platelet receptors and purified GPIIb/IIIa platelet receptors, with a selected fibrinogen receptor antagonist to form a GPIIb/IIIa receptor:GPIIb/IIIa receptor antagonist complex.

The method for identifying a patient at risk comprises incubating patient plasma with a GPIIb/IIIa receptor:GPIIb/IIIa receptor antagonist complex to form a GPIIb/IIIa receptor:GPIIb/IIIa receptor antagonist:plasma antibody complex, incubating the GPIIb/IIIa receptor:GPIIb/IIIa receptor antagonist:plasma antibody complex with a secondary anti-human detectable antibody to form a GPIIb/IIIa receptor:GPIIb/IIIa receptor antagonist:plasma antibody:secondary anti-human detectable antibody complex, and detecting the presence of the secondary anti-human detectable antibody in the GPIIb/IIIa receptor:GPIIb/IIIa receptor antagonist:plasma antibody:secondary anti-human detectable antibody complex.

In the method of the invention, the GPIIb/IIIa receptor:GPIIb/IIIa receptor antagonist complex is incubated with the patient's plasma. Patient plasma which contains antagonist-dependent antibodies will induce formation of a GPIIb/IIIa receptor:GPIIb/IIIa receptor antagonist:plasma antibody complex. Plasma which does not contain antagonist-dependent antibodies will not form a GPIIb/IIIa receptor:GPIIb/IIIa receptor antagonist:plasma antibody complex after this incubation step. The material formed following the incubation step is washed to remove substances which do not associate with the formed GPIIb/IIIa receptor:GPIIb/IIIa receptor antagonist:plasma antibody complex.

The material formed following the above-described incubation step is then incubated with a secondary anti-human detectable antibody (e.g. antihuman IgG, antihuman IgM, antihuman IgA, associated with a detectable marker such as a fluorescent label or an enzyme (e.g. horseradish peroxidase, which induces a detectable reaction when exposed to a substrate that is acted upon by the enzyme)). If a GPIIb/IIIa receptor:GPIIb/IIIa receptor antagonist:plasma antibody complex forms following addition of the patient's plasma, then the secondary anti-human detectable antibody will complex with the GPIIb/IIIa receptor:GPIIb/IIIa receptor antagonist:plasma antibody complex, and will not be washed away during a washing step. If a GPIIb/IIIa receptor:GPIIb/IIIa receptor antagonist:plasma antibody complex does not form following addition of the patient's plasma, then the secondary antibody will not complex with the GPIIb/IIIa receptor:GPIIb/IIIa receptor antagonist complex, and will be washed away during a subsequent washing step. Detection of the presence of the GPIIb/IIIa receptor:GPIIb/IIIa receptor antagonist:plasma antibody:secondary anti-human detectable antibody complex is an indication that the patient does have antagonist-dependent antibodies reactive with platelets and that the patient is at risk to developing thrombocytopenia following consumption of the selected fibrinogen receptor antagonist. The absence of the GPIIb/IIIa receptor:GPIIb/IIIa receptor antagonist:plasma antibody:secondary anti-human detectable antibody complex indicates that the GPIIb/IIIa receptor:GPIIb/IIIa receptor antagonist:plasma antibody complex did not form, and that the patient is not at risk to developing fibrinogen receptor antagonist induced thrombocytopenia.

More particularly, the secondary anti-human detectable antibody is, for example, a fluorescence-labeled F(ab')2 anti-IgG, fluorescence-labeled F(ab')2 anti-IgM, fluorescence-labeled F(ab')2 anti-IgA, enzyme labeled IgG, enzyme labeled IgM, or enzyme labeled IgA. The fluorescence-labeled F(ab')2 anti-IgG, fluorescence-labeled F(ab')2 anti-IgM, fluorescence-labeled F(ab')2 anti-IgA antibodies may be suitably labeled with flourescein. The enzyme labeled IgG, enzyme labeled IgM, and enzyme labeled IgA antibodies may be suitably labeled with an enzyme such as horseradish peroxidase.

The invention also is a method for identifying a patient not at risk to developing fibrinogen receptor antagonist-induced thrombocytopenia which comprises reacting patient plasma with a GPIIb/IIIa receptor:GPIIb/IIIa receptor antagonist complex to form a first reaction product, reacting the first reaction product with a secondary anti-human detectable antibody to form a second reaction product, washing substances from the second reaction product which do not complex with the GPIIb/IIIa receptor:GPIIb/IIIa receptor antagonist complex to form a washed second reaction product, and detecting the absence of the secondary anti-human detectable antibody in the washed second reaction product.

The selected GP IIb/IIIa receptor antagonist suitable for the methods of the invention is any antagonist which is useful for inhibiting fibrinogen binding to the GP IIb/IIIa platelet receptor. Such antagonists are well known in the art Antagonists for the GP IIb/IIIa receptor have been described in, for example, U.S. Pat. Nos. 5,470,849, 5,463,011, 5,455,243, 5,451,578, 5,446,056, 5,441,952, 5,422,249, 5,416,099, 5,405,854, 5,397,791, 5,393,760, 5,389,631, 5,380,713, 5,374,622, 5,358,956, 5,344,783, 5,340,798, 5,338,7235,334,596, 5,321,034, 5,318,899 (e.g. cyclic heptapeptides Mpr-(Acetimidyl-Lys)-Gly-Asp-Trp-Phe-Cys-NH$_2$, Mpr-(Acetimidyl-Lys)-Gly-Asp-Trp-Phe-Pen-NH$_2$, Mpr-(Phenylimidyl-Lys)-Gly-Asp-Trp-Phe-Pen-NH$_2$, and Mpr-(Phenylimidyl-Lys)-Gly-Asp-Trp-Phe-Cys-NH$_2$, wherein Mpr is mercapto propionyl), 5,312,923, 5,294,616, 5,292,756 (e.g. 2-S-(n-Butylsulfonylamino)-3[4-piperidin-4yl)butyloxyphenyl]propionic acid hydrochloride), 5,281,585 5,272,158, 5,264,420, 5,260,307, 5,239,113 (e.g. Ethyl 3-[[4-[[4-(aminoiminomethyl)phenyl]amino]-1,4-dioxobutyl]amino]-4-pentynoate), 5,227,490, 5,206,373, 4,703,036 (e.g. N-Methyl-D-phenylalanyl-N-[(1S)-1formyl-4-guanidinobutyl]-L-prolinamide), EP 505 868 (e.g. ((1-(2-((4-(aminoiminomethyl)benzoyl)amino)-3-(4-hydroxyphenyl)-1-oxopropyl)-4-piperidinyl)oxy)-(S)-acetic acid), WO 9311152 (e.g. N-(2-(2-(((3-((aminoiminomethyl)amino)propyl)amino)-carbonyl)-1-piperidnyl)-1-(cyclohexylmethyl)-2-oxoethyl)-(R,S)-glycine), WO 9418981 (e.g. 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid), WO 9514683 (e.g. methyl-N$^3$-[2-{3-(4-formamidinophenyl)-isoxazolin-5(R)-yl}-acetyl]-N$^2$-(n-butyloxycarbonyl)-2,3-(S)-diaminopropionate acetate salt), EP 333.356 and WO 9422820. They are described as useful for inhibiting fibrinogen binding and inhibiting clot formation.

EXAMPLE 1

GP IIb/IIIa Antagonist Treatment and Method for Identifying a Patient at Risk to Developing GP IIb/IIIa Antagonist-induced Thrombocytopenia A patient with acute coronary ischemic syndromes receives coronary revascularization with angioplasty. Aspirin is administered in a dose of 325 mg at least two hours before angioplasty, and daily thereafter. Heparin is given intravenously in an initial bolus dose of 10,000 to 12,000 units followed by incremental bolus doses of up to 3000 units at 15-minute intervals, but no more than 20,000 units is given during the procedure. The goal is to keep the activated clotting time between 300 and 350 seconds during the operation. Heparin is continued by constant infusion for at least 12 hours to maintain the activated partial-thromboplastin time at 1.5 to 2.5 times the control value. Aspirin is required at discharge in a dose of 325 mg per day.

The patient is scheduled to receive an oral tablet containing 15 mg of the fibrinogen receptor gp IIb/IIIa antagonist 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid (compound 1-1), described in WO 94/18981. Prior to initiation of treatment with compound 1-1 the patient is screened to determine whether the patient is at risk to developing thrombocytopenia induced by compound 1—1. A plasma sample is drawn from the patient and incubated with a GPIIb/IIIa receptor:compound 1-1 complex to bind antagonist-dependent plasma antibodies to the complex and form a GPIIb/IIIa receptor:compound 1-1:plasma antibody complex. The GPIIb/IIIa receptor:compound 1-1:plasma antibody complex is incubated with horseradish peroxidase anti-human IgG to form a GPIIb/IIIa receptor:compound 1-1:plasma antibody:horseradish peroxidase anti-human IgG complex. The presence of the horseradish peroxidase anti-human IgG in the GPIIb/IIIa receptor:compound 1-1:plasma antibody:horseradish peroxidase anti-human IgG complex is detected by observing a horseradish peroxidase-induced enzyme reaction, which confirms the presence of plasma antibodies associated with a thrombocytopenic reaction to the GPIIb/IIIa receptor:compound 1-1 complex. Thus, the patient is determined to be at risk to developing antagonist-induced thrombocytopenia.

EXAMPLE 2

GP IIb/IIIa Antagonist Treatment and Method for Identifying a Patient not at Risk to Developing GP IIb/IIIa Antagonist-induced Thrombocytopenia A patient with acute coronary ischemic syndromes receives coronary revascularization with angioplasty. Aspirin is administered in a dose of 325 mg at least two hours before angioplasty, and daily thereafter. Heparin is given intravenously in an initial bolus dose of 10,000 to 12,000 units followed by incremental bolus doses of up to 3000 units at 15-minute intervals, but no more than 20,000 units is given during the procedure. The goal is to keep the activated clotting time between 300 and 350 seconds during the operation. Heparin is continued by constant infusion for at least 12 hours to maintain the activated partial-thromboplastin time at 1.5 to 2.5 times the control value. Aspirin is required at discharge in a dose of 325 mg per day.

The patient is scheduled to receive an oral tablet containing 15 mg of the fibrinogen receptor gp IIb/IIIa antagonist 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid (compound 1-1), described in WO 94/18981. Prior to initiation of treatment with compound 1-1, the patient is screened to determine whether the patient is at risk to developing thrombocytopenia induced by compound 1—1. A plasma sample is drawn from the patient and incubated with a GPIIb/IIIa receptor:compound 1-1 complex to attempt to bind antagonist-dependent plasma antibodies to the complex and form a GPIIb/IIIa receptor:compound 1—1:plasma antibody complex. However, no patient plasma antibodies are present, and the GPIIb/IIIa receptor:compound 1—1:plasma antibody complex does not form. The GPIIb/IIIa receptor:compound 1-1 complex is incubated with horseradish peroxidase anti-human IgG. Since no plasma antibody complex formed, the horseradish peroxidase anti-human IgG does not associate with the GPIIb/IIIa receptor:compound 1-1 complex. The horseradish peroxidase anti-human IgG is washed away because it does not complex with the GPIIb/IIIa receptor:compound 1-1 complex. Exposure of the GPIIb/IIIa receptor:compound 1-1 complex to conditions that would identify the presence of the horseradish peroxidase anti-human IgG indicate that no enzyme is present and that the patient plasma does not have plasma antibodies associated with compound 1-1-induced thrombocytopenia, and that the patient is not at risk to developing thrombocytopenia.

What is claimed is:

1. A method for identifying a patient at risk to developing fibrinogen receptor antagonist-induced thrombocytopenia, which patient does not have thrombocytopenia, which comprises incubating patient plasma with a GPIIb/IIIa receptor:GPIIb/IIIa receptor antagonist complex to form a GPIIb/IIIa receptor:GPIIb/IIIa receptor antagonist:plasma antibody complex, incubating the GPIIb/IIIa receptor:GPIIb/IIIa receptor antagonist:plasma antibody complex with a secondary anti-human detectable antibody to form a GPIIb/IIIa receptor:GPIIb/IIIa receptor antagonist:plasma antibody:secondary anti-human detectable antibody complex, and detecting the presence of the secondary anti-human detectable antibody in the GPIIb/IIIa receptor:GPIIb/IIIa receptor antagonist:plasma antibody:secondary anti-human detectable antibody complex which signifies interaction between the GPIIb/IIIa receptor:GPIIb/IIIa receptor antagonist complex and a patient plasma antibody and identifies the patient as at risk to developing thrombocytopenia following treatment with the GPIIb/IIIa receptor antagonist.

2. A method of claim 1 wherein the antagonist is selected from the group consisting of Mpr-(Acetimidyl-Lys)-Gly-Asp-Trp-Phe-Cys-NH$_2$,
Mpr-(Acetimidyl-Lys)-Gly-Asp-Trp-Phe-Pen-NH$_2$,
Mpr-(Phenylimidyl-Lys)-Gly-Asp-Trp-Phe-Pen-NH$_2$,
Mpr-(Phenylimidyl-Lys)-Gly-Asp-Trp-Phe-Cys-NH$_2$,
N-Methyl-D-phenylalanyl-N-[(1S)-1-formyl-4-guanidinobutyl]-L-prolinamide,
((1-(2-((4-(aminoiminomethyl)benzoyl)amino)-3-(4-hydroxyphenyl)-1-oxopropyl)-4-piperidinyl)oxy)-(S)-acetic acid,
Ethyl 3-[[4-[[4-(aminoiminomethyl)phenyl]amino]-1,4-dioxobutyl]amino]-4-pentynoate,
N-(2-(2-(((3-((aminoiminomethyl)amino)propyl)amino) carbonyl)-1-piperidnyl)-1-(cyclohexylmethyl)-2-oxoethyl)-(R,S)-glycine,
(2-S-(n-Butylsulfonylamino)-3[4-(piperidin-4-yl) butyloxyphenyl]propionic acid hydrochloride,
Ethyl 3-[[4-[[4-(aminoiminomethyl)phenyl]amino]-1,4-dioxobutyl]amino]-4-pentynoate,
2(S)-[(p-Toluenesulfonyl)amino]-3-[[[5,6,7,8-tetrahydro-4-oxo-5-[2-(piperidin-4-yl)ethyl]-4H-pyrazolo-[1,5-a] [1,4]diazepin-2-yl]carbonyl]-amino]propionic acid,
(R)-methyl-3-[[[3-[4-(aminoiminomethyl)phenyl]-4,5-dihydro-5-isoxazolyl]acetyl]amino]-N-(butoxycarbonyl)-L-alanine monoacetate, and pharmaceutically acceptable salts thereof.

3. A method of claim 2 wherein the secondary anti-human detectable antibody is selected from fluorescence-labeled F(ab')2 anti-IgG, fluorescence-labeled F(ab')2 anti-IgM, fluorescence-labeled F(ab')2 anti-IgA, enzyme labeled IgG, enzyme labeled IgM, and enzyme labeled IgA.

4. A method of claim 3 wherein the fluorescence-labeled F(ab')2 anti-IgG, fluorescence-labeled F(ab')2 anti-IgM, fluorescence-labeled F(ab')2 anti-IgA antibodies are labeled with flourescein.

5. A method of claim 3 wherein the enzyme labeled IgG, enzyme labeled IgM, and enzyme labeled IgA antibodies are labeled with horseradish peroxidase.

6. A method for identifying a patient not at risk to developing fibrinogen receptor antagonist-induced thrombocytopenia which comprises incubating patient plasma with a GPIIb/IIIa receptor:GPIIb/IIIa receptor antagonist complex to form a first reaction product, incubating the first reaction product with a secondary anti-human detectable antibody to form a second reaction product, washing substances from the second reaction product which do not complex with the GPIIb/IIIa receptor:GPIIb/IIIa receptor antagonist complex to form a washed second reaction product, and detecting the absence of the secondary anti-human detectable antibody in the washed second reaction product which signifies that the patient is not at risk to developing fibrinogen receptor antagonist-induced thrombocytopenia.

* * * * *